US011765478B2

(12) United States Patent
Saito et al.

(10) Patent No.: US 11,765,478 B2
(45) Date of Patent: Sep. 19, 2023

(54) IMAGING SYSTEM AND ENDOSCOPE SYSTEM

(71) Applicant: OLYMPUS CORPORATION, Hachioji (JP)

(72) Inventors: Masashi Saito, Tokyo (JP); Yoshio Hagihara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 516 days.

(21) Appl. No.: 17/078,427

(22) Filed: Oct. 23, 2020

(65) Prior Publication Data
US 2021/0044770 A1 Feb. 11, 2021

Related U.S. Application Data

(63) Continuation of application No. PCT/JP2018/017181, filed on Apr. 27, 2018.

(51) Int. Cl.
H04N 1/00 (2006.01)
A61B 1/00 (2006.01)
(Continued)

(52) U.S. Cl.
CPC ....... *H04N 25/709* (2023.01); *A61B 1/00004* (2013.01); *G02B 23/24* (2013.01);
(Continued)

(58) Field of Classification Search
CPC ........ H04N 1/00; H04N 1/032; H04N 1/0083; H04N 1/00347; H04N 1/00095;
(Continued)

(56) References Cited

U.S. PATENT DOCUMENTS 9,198,557 B2 * 12/2015 Takizawa ........... A61B 1/00013
10,506,917 B2 * 12/2019 Adachi .............. A61B 1/00029
(Continued)

FOREIGN PATENT DOCUMENTS

EP 3 187 097 A1 7/2017
JP 5-83689 A 4/1993
(Continued)

OTHER PUBLICATIONS

International Search Report dated Jul. 24, 2018, issued in counterpart International Application No. PCT/JP2018/017181, with English Translation. (4 pages).

*Primary Examiner* — Hai L Nguyen
(74) *Attorney, Agent, or Firm* — WHDA, LLP

(57) ABSTRACT

In an imaging system, a differential signal transmission circuit is configured to output a first signal to a first signal line in an image output period and is configured to output a second signal to a second signal line in the image output period. The first signal and the second signal are included in a differential signal. A signal output circuit is configured to output a second clock signal to the first signal line in a blanking period different from the image output period and is configured to output a second control signal to the second signal line in the blanking period. In a PLL, connection between a charge pump and a loop filter is controlled on the basis of the second control signal output to the second signal line.

9 Claims, 6 Drawing Sheets

(51) Int. Cl.
    *G02B 23/24*    (2006.01)
    *H04N 25/709*   (2023.01)
    *H03L 7/089*    (2006.01)
    *H03L 7/099*    (2006.01)
    *H04N 7/18*     (2006.01)
    *H03L 7/10*     (2006.01)
    *A61B 1/05*     (2006.01)

(52) U.S. Cl.
    CPC ............ *H03L 7/0891* (2013.01); *H03L 7/099* (2013.01); *H03L 7/104* (2013.01); *H04N 7/18* (2013.01); *A61B 1/05* (2013.01)

(58) Field of Classification Search
    CPC ........... H04N 1/00114; H04N 1/00127; H04N 1/00129; A61B 1/00002; A61B 1/00004; A61B 1/00006; A61B 1/00009; G02B 23/24; G02B 23/2407; G02B 23/2415; G02B 23/2484
    USPC .................. 600/101, 103, 109, 112, 118
    See application file for complete search history.

(56)       References Cited

U.S. PATENT DOCUMENTS

2014/0194686 A1   7/2014   Murayama
2014/0241335 A1   8/2014   Chen et al.

FOREIGN PATENT DOCUMENTS

| JP | 11-252438 A    | 9/1999  |
| JP | 2004-81748 A   | 3/2004  |
| JP | 2007-37569 A   | 2/2007  |
| JP | 2013-248277 A  | 12/2013 |
| JP | 2014-147667 A  | 8/2014  |
| JP | 2015-188262 A  | 10/2015 |
| WO | 2016/104369 A1 | 6/2016  |
| WO | 2017/122626 A1 | 7/2017  |

* cited by examiner

IMAGING SYSTEM AND ENDOSCOPE SYSTEM

The present application is a continuation application based on International Patent Application No. PCT/JP2018/017181 filed on Apr. 27, 2018, the content of which is incorporated herein by reference.

BACKGROUND OF THE INVENTION

Field of the Invention

The present invention relates to an imaging system and an endoscope system.

Description of Related Art

An imaging system that transmits an image signal through a long cable has been developed. The imaging system includes a camera unit and a main body. In the imaging system, it is necessary to supply a clock signal to an imaging device.

In an endoscope system disclosed in Japanese Unexamined Patent Application, First Publication No. 2015-188262, a camera unit (endoscope) and a main body (processor) are connected to each other by a transmission cable. The transmission cable transmits an image signal, a reference clock signal, and a synchronizing signal in addition to a power source voltage and a ground voltage. The image signal, the reference clock signal, and the synchronizing signal are transmitted by different cables.

SUMMARY OF THE INVENTION

According to a first aspect of the present invention, an imaging system includes a camera unit and a main body. The camera unit includes a phase locked loop (PLL), a signal generation circuit, a solid-state imaging device, and a differential signal transmission circuit. The PLL is configured to generate a first clock signal. The signal generation circuit is configured to generate a first control signal on the basis of the first clock signal. The solid-state imaging device is configured to generate an image signal on the basis of the first control signal. The differential signal transmission circuit is configured to output a first signal generated on the basis of the image signal to a first signal line in an image output period and is configured to output a second signal generated on the basis of the image signal to a second signal line different from the first signal line in the image output period. The first signal and the second signal are a pair included in a differential signal. The main body includes a differential signal reception circuit and a signal output circuit. The differential signal reception circuit is configured to receive the first signal output to the first signal line and the second signal output to the second signal line. The signal output circuit is configured to output a second clock signal to the first signal line in a blanking period different from the image output period and is configured to output a second control signal to the second signal line in the blanking period. The PLL includes a phase comparator, a charge pump, a loop filter, and a voltage-controlled oscillator. The second clock signal output to the first signal line is input to the phase comparator. The phase comparator is configured to compare a phase of the first clock signal with a phase of the second clock signal and is configured to generate a digital signal that represents a difference between the phase of the first clock signal and the phase of the second clock signal. The charge pump is configured to generate an analog signal on the basis of the digital signal. The loop filter is electrically insulated from the charge pump in the image output period. The loop filter is electrically connected to the charge pump in the blanking period on the basis of the second control signal output to the second signal line. The loop filter is configured to generate an analog voltage signal on the basis of the analog signal. The voltage-controlled oscillator is configured to generate the first clock signal on the basis of the analog voltage signal.

According to a second aspect of the present invention, an imaging system includes a camera unit and a main body. The camera unit includes a phase locked loop (PLL), a first signal generation circuit, a solid-state imaging device, a differential signal transmission circuit, and a second signal generation circuit. The PLL is configured to generate a first clock signal. The first signal generation circuit is configured to generate a first control signal on the basis of the first clock signal. The solid-state imaging device is configured to generate an image signal on the basis of the first control signal. The differential signal transmission circuit is configured to output a first signal generated on the basis of the image signal to a first signal line in an image output period and is configured to output a second signal generated on the basis of the image signal to a second signal line different from the first signal line in the image output period. The first signal and the second signal are a pair included in a differential signal. The main body includes a differential signal reception circuit and a signal output circuit. The differential signal reception circuit is configured to receive the first signal output to the first signal line and the second signal output to the second signal line. The signal output circuit is configured to output a second clock signal to the first signal line in a blanking period different from the image output period and is configured to output a third clock signal to the second signal line in the blanking period. The second signal generation circuit is configured to generate a second control signal on the basis of the second clock signal output to the first signal line and the third clock signal output to the second signal line. The PLL includes a phase comparator, a charge pump, a loop filter, and a voltage-controlled oscillator. The second clock signal output to the first signal line is input to the phase comparator. The phase comparator is configured to compare a phase of the first clock signal with a phase of the second clock signal and is configured to generate a digital signal that represents a difference between the phase of the first clock signal and the phase of the second clock signal. The charge pump is configured to generate an analog signal on the basis of the digital signal. The loop filter is electrically insulated from the charge pump in the image output period. The loop filter is electrically connected to the charge pump in the blanking period on the basis of the second control signal. The loop filter is configured to generate an analog voltage signal on the basis of the analog signal. The voltage-controlled oscillator is configured to generate the first clock signal on the basis of the analog voltage signal.

According to a third aspect of the present invention, in the first or second aspect, the PLL may further include a switch electrically connected to the charge pump and the loop filter. The switch may be configured to be turned off in the image output period and thus electrically insulate the loop filter from the charge pump. The switch is configured to be turned on in the blanking period and thus electrically connect the loop filter to the charge pump.

According to a fourth aspect of the present invention, in the third aspect, the imaging system may further include a logical circuit electrically connected to the switch and the second signal line. A threshold voltage of the logical circuit may be outside a range of a voltage of the first signal and the second signal.

According to a fifth aspect of the present invention, in any one of the first to fourth aspects, the phase comparator may be configured to generate the digital signal in the blanking period. The charge pump may be configured to generate the analog signal in the blanking period. The loop filter may be configured to hold the analog voltage signal in the image output period. The voltage-controlled oscillator may be configured to generate the first clock signal in the blanking period and the image output period.

According to a sixth aspect of the present invention, an endoscope system includes a scope and the imaging system in any one of the first to fifth aspects. The scope includes a tip end and a base end. The solid-state imaging device is disposed in the tip end. The main body is connected to the base end.

DETAILED DESCRIPTION OF THE INVENTION

Hereinafter, embodiments of the present invention will be described with reference to the drawings. Each embodiment will be described in detail by using an electronic endoscope system as an example of an imaging system.

First Embodiment

Figure 1:
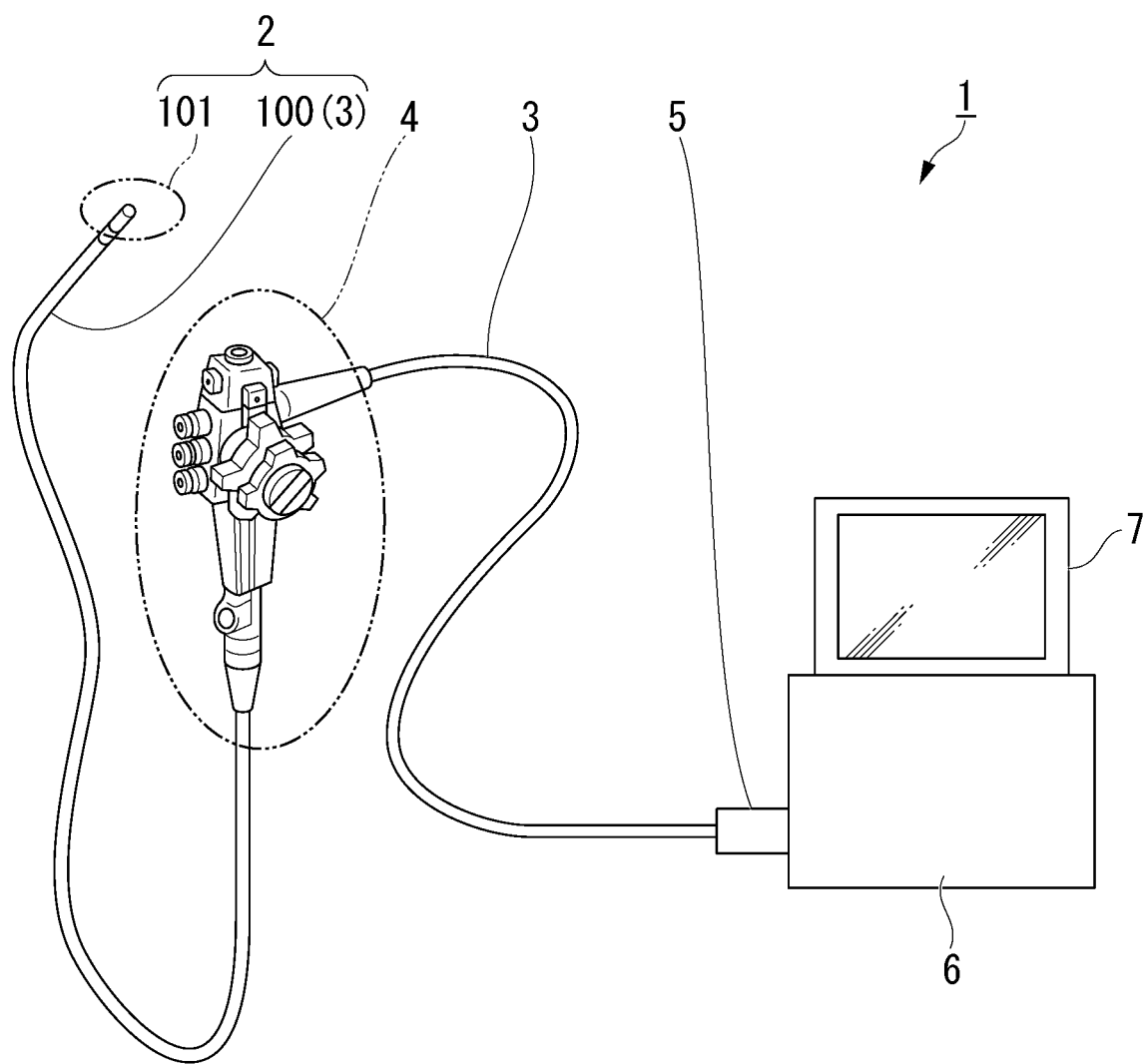
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute an endoscope.

Figure 2:
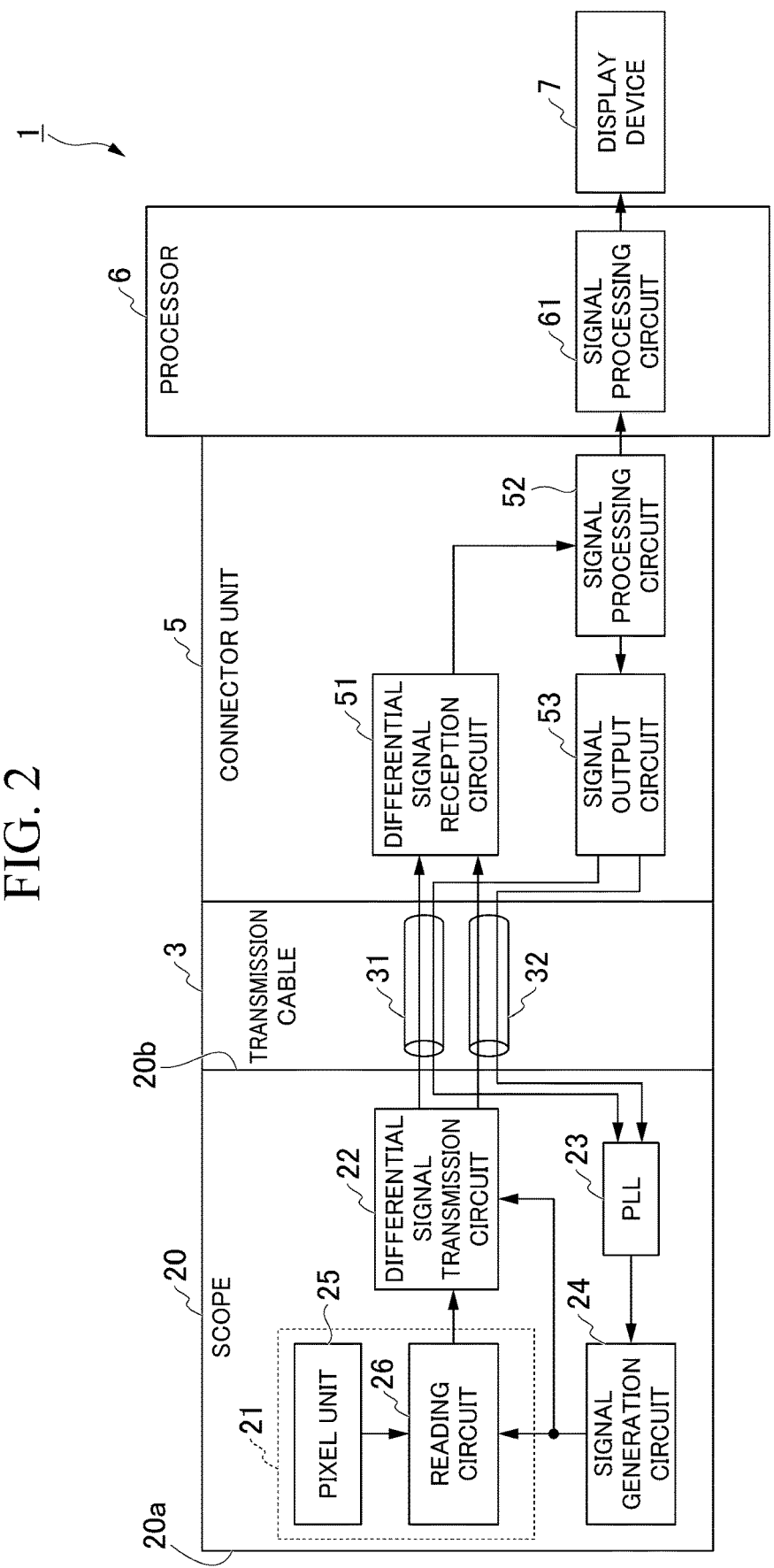
FIG. 2 is a block diagram showing a configuration of the endoscope system according to the first embodiment of the present invention.

The endoscope insertion unit 2 includes an insertion unit 100 that is to be inserted into a subject. The insertion unit 100 is part of the transmission cable 3. The insertion unit 100 is to be inserted inside the subject. The endoscope insertion unit 2 generates an image signal (image data) by imaging the inside of the subject. The endoscope insertion unit 2 outputs the generated image signal to the processor 6. A scope 20 shown in FIG. 2 is disposed in a tip end part 101 of the insertion unit 100. In the insertion unit 100, the operation unit 4 is connected to the end part opposite to the tip end part 101. The operation unit 4 accepts a variety of operations for the endoscope insertion unit 2.

The transmission cable 3 connects the scope 20 of the endoscope insertion unit 2 and the connector unit 5 together. The image signal generated by the scope 20 is output to the connector unit 5 via the transmission cable 3.

The connector unit 5 is connected to the endoscope insertion unit 2 and the processor 6. The connector unit 5 performs predetermined signal processing on the image signal output from the endoscope insertion unit 2. The connector unit 5 outputs the image signal to the processor 6.

The processor 6 performs predetermined image processing on the image signal output from the connector unit 5. Furthermore, the processor 6 centrally controls the entire endoscope system 1.

The display device 7 displays an image on the basis of the image signal processed by the processor 6. In addition, the display device 7 displays various pieces of information related to the endoscope system 1.

The endoscope system 1 includes a light source device that generates illumination light emitted to the subject. The light source device is not shown in FIG. 1.

FIG. 2 shows an internal configuration of the endoscope system 1. The endoscope system 1 shown in FIG. 2 includes the scope 20, the transmission cable 3, the connector unit 5, the processor 6, and the display device 7.

The scope 20 is a camera unit. The scope 20 includes an imaging device 21, a differential signal transmission circuit 22, a phase locked loop (PLL) 23, and a signal generation circuit 24 (first signal generation circuit). The imaging device 21 includes a pixel unit 25 and a reading circuit 26. The scope 20 has a function of an imaging apparatus. The transmission cable 3 includes a first signal line 31 and a second signal line 32. The connector unit 5 and the processor 6 are a main body. The connector unit 5 includes a differential signal reception circuit 51, a signal processing circuit 52, and a signal output circuit 53. The processor 6 includes a signal processing circuit 61.

A schematic configuration of the endoscope system 1 will be described. The PLL 23 generates a first clock signal. The signal generation circuit 24 generates a first control signal on the basis of the first clock signal. The imaging device 21 is a solid-state imaging device. The imaging device 21 generates an image signal on the basis of the first control signal. The differential signal transmission circuit 22 outputs a first signal generated on the basis of the image signal to the first signal line 31 in an image output period. The differential signal transmission circuit 22 outputs a second signal generated on the basis of the image signal to the second signal line 32 in the image output period. The second signal line 32 is different from the first signal line 31. The first signal and the second signal are a pair included in a differential signal. The differential signal reception circuit 51 receives the first signal output to the first signal line 31 and the second signal output to the second signal line 32. The signal output circuit 53 outputs a second clock signal to the first signal line 31 in a blanking period excluding the image output period. The signal output circuit 53 outputs a second control signal to the second signal line 32 in the blanking period.

The scope 20 includes a tip end part 20a and a base end part 20b. The imaging device 21 is disposed in the tip end part 20a. The processor 6 is connected to the base end part 20b.

A detailed configuration of the endoscope system 1 will be described. The pixel unit 25 includes a plurality of pixels.

The pixel unit 25 generates a pixel signal that is based on light incident to the pixel unit 25. The reading circuit 26 reads the pixel signal generated by the pixel unit 25 from the pixel unit 25. The imaging device 21 generates an image signal by performing noise reduction, signal amplification, analog-to-digital conversion (AD conversion), and the like on the pixel signal. The image signal generated by the imaging device 21 is output to the differential signal transmission circuit 22. The image signal input to the differential signal transmission circuit 22 is a single-ended signal.

The differential signal transmission circuit 22 generates a differential signal on the basis of the image signal. The differential signal includes a first signal and a second signal. When the state of one of the first signal and the second signal is a high level, the state of the other of the first signal and the second signal is a low level. For example, the differential signal transmission circuit 22 and the differential signal reception circuit 51 perform communication of the differential signal on the basis of the low voltage differential signaling (LVDS). The differential signal transmission circuit 22 is electrically connected to the first signal line 31 and the second signal line 32. The differential signal transmission circuit 22 outputs the first signal to the first signal line 31 and outputs the second signal to the second signal line 32.

The connector unit 5 electrically connects the endoscope insertion unit 2 (scope 20) and the processor 6 together. The connector unit 5 and the scope 20 are connected to each other by the transmission cable 3. The connector unit 5 and the processor 6 are connected to each other by a coil cable. The processor 6 is connected to the base end part 20b of the scope 20 via the transmission cable 3 and the connector unit 5.

The differential signal reception circuit 51 is electrically connected to the first signal line 31 and the second signal line 32. The differential signal reception circuit 51 receives the first signal that has passed through the first signal line 31 and receives the second signal that has passed through the second signal line 32. The differential signal reception circuit 51 generates a single-ended image signal on the basis of the first signal and the second signal. The differential signal reception circuit 51 outputs the image signal to the signal processing circuit 52.

The signal processing circuit 52 performs predetermined signal processing on the image signal. The signal processing circuit 52 outputs the processed image signal to the processor 6. In addition, the signal processing circuit 52 generates the second clock signal and the second control signal. The second clock signal is a reference clock signal. The signal processing circuit 52 outputs the generated second clock signal and the generated second control signal to the signal output circuit 53. The signal output circuit 53 is electrically connected to the first signal line 31 and the second signal line 32. The signal output circuit 53 outputs the second clock signal to the first signal line 31 and outputs the second control signal to the second signal line 32.

The PLL 23 is electrically connected to the first signal line 31 and the second signal line 32. The second clock signal that has passed through the first signal line 31 and the second control signal that has passed through the second signal line 32 are input to the PLL 23. The PLL 23 generates the first clock signal on the basis of the second clock signal. The first clock signal is synchronized with the second clock signal. The operation of the PLL 23 is controlled on the basis of the second control signal. The PLL 23 outputs the generated first clock signal to the signal generation circuit 24.

The signal generation circuit 24 generates a timing signal on the basis of the first clock signal. For example, the timing signal includes a horizontal synchronizing signal and a vertical synchronizing signal. The signal generation circuit 24 outputs the generated timing signal to the reading circuit 26 and the differential signal transmission circuit 22. The reading circuit 26 reads the pixel signal on the basis of the timing signal. The imaging device 21 reads the pixel signal on the basis of the timing signal and generates the image signal on the basis of the timing signal. The differential signal transmission circuit 22 transmits the differential signal on the basis of the timing signal.

The imaging device 21 stops generation of the image signal in the blanking period. In the blanking period, output of valid image data from the imaging device 21 is stopped. The blanking period intermittently occurs. The imaging device 21 generates the image signal that is based on the pixel signal read from a pixel 111 of one row in a period between two blanking periods.

The signal processing circuit 61 performs predetermined image processing on the image signal processed by the signal processing circuit 52. The predetermined image processing includes synchronization processing, white balance (WB) adjustment processing, gain adjustment processing, gamma correction processing, digital-to-analog (D/A) conversion processing, format conversion processing, and the like. The signal processing circuit 61 outputs the processed image signal to the display device 7.

The display device 7 displays an image on the basis of the image signal output from the signal processing circuit 61. The display device 7 includes a display panel of liquid crystal, electro luminescence, or the like.

In the scope 20, the differential signal transmission circuit 22, the PLL 23, and the signal generation circuit 24 are disposed outside the imaging device 21. At least one of the differential signal transmission circuit 22, the PLL 23, and the signal generation circuit 24 may be disposed inside the imaging device 21.

Figure 3:
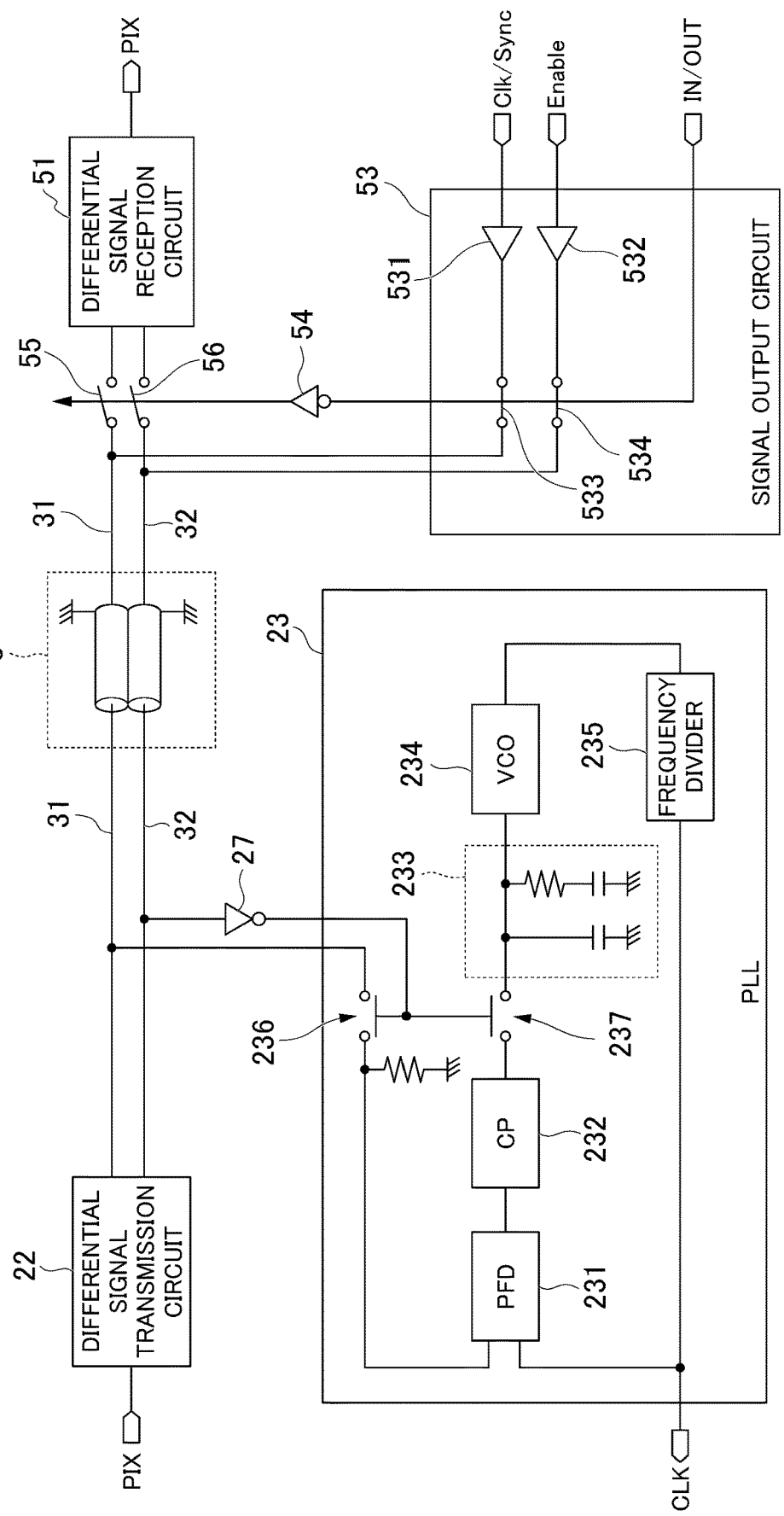
FIG. 3 is a block diagram showing a configuration of a main part of the endoscope system according to the first embodiment of the present invention.

FIG. 3 shows a configuration of a main part of the endoscope system 1. The signal output circuit 53 includes a buffer 531, a buffer 532, a switch 533, and a switch 534. The PLL 23 includes a phase comparator 231, a charge pump 232, a loop filter 233, a voltage-controlled oscillator (VCO) 234, a frequency divider 235, a switch 236, and a switch 237.

The signal processing circuit 52 generates a second clock signal Clk/Sync, a second control signal Enable, and a switching signal IN/OUT. The signal processing circuit 52 outputs the second clock signal Clk/Sync, the second control signal Enable, and the switching signal IN/OUT to the signal output circuit 53. The second clock signal Clk/Sync is input to the buffer 531. The second control signal Enable is input to the buffer 532. The buffer 531 outputs the second clock signal Clk/Sync to the switch 533. The buffer 532 outputs the second control signal Enable to the switch 534.

The switch 533 is connected to the buffer 531 and the first signal line 31. The switch 534 is connected to the buffer 532 and the second signal line 32. The switch 533 and the switch 534 are an element that is able to switch between an ON state and an OFF state. The switch 533 and the switch 534 are either turned on or turned off. The state of the switch 533 and the switch 534 is controlled on the basis of the switching signal IN/OUT.

When the switch 533 is in the ON state, the buffer 531 and the first signal line 31 are electrically connected to each other. At this time, the second clock signal Clk/Sync is output to the first signal line 31. When the switch 533 is in the OFF state, the buffer 531 and the first signal line 31 are electrically insulated from each other. At this time, output of the second clock signal Clk/Sync to the first signal line 31 is stopped. The switch 533 is in the ON state in the blanking period and the switch 533 is in the OFF state in the image output period.

When the switch 534 is in the ON state, the buffer 532 and the second signal line 32 are electrically connected to each other. At this time, the second control signal Enable is output to the second signal line 32. When the switch 534 is in the OFF state, the buffer 532 and the second signal line 32 are electrically insulated from each other. At this time, output of the second control signal Enable to the second signal line 32 is stopped. The switch 534 is in the ON state in the blanking period and the switch 534 is in the OFF state in the image output period.

The signal output circuit 53 outputs the switching signal IN/OUT. The switching signal IN/OUT is input to an inverter 54. The inverter 54 inverts the logical state of the switching signal IN/OUT. The inverter 54 outputs the switching signal IN/OUT to a switch 55 and a switch 56. The inverter 54, the switch 55, and the switch 56 are disposed in the connector unit 5.

The switch 55 is connected to the first signal line 31 and the differential signal reception circuit 51. The switch 56 is connected to the second signal line 32 and the differential signal reception circuit 51. The switch 55 and the switch 56 are an element that is able to switch between an ON state and an OFF state. The switch 55 and the switch 56 are either turned on or turned off. The state of the switch 55 and the switch 56 is controlled on the basis of the switching signal IN/OUT.

When the switch 55 is in the ON state, the first signal line 31 and the differential signal reception circuit 51 are electrically connected to each other. At this time, the first signal is input to the differential signal reception circuit 51. When the switch 55 is in the OFF state, the first signal line 31 and the differential signal reception circuit 51 are electrically insulated from each other. At this time, input of the first signal to the differential signal reception circuit 51 is stopped. The switch 55 is in the ON state in the image output period and the switch 55 is in the OFF state in the blanking period.

When the switch 56 is in the ON state, the second signal line 32 and the differential signal reception circuit 51 are electrically connected to each other. At this time, the second signal is input to the differential signal reception circuit 51. When the switch 56 is in the OFF state, the second signal line 32 and the differential signal reception circuit 51 are electrically insulated from each other. At this time, input of the second signal to the differential signal reception circuit 51 is stopped. The switch 56 is in the ON state in the image output period and the switch 56 is in the OFF state in the blanking period.

The second clock signal Clk/Sync output to the first signal line 31 is input to the phase comparator 231. The phase comparator 231 compares the phase of a first clock signal CLK with the phase of the second clock signal Clk/Sync. The phase comparator 231 generates a digital signal that represents the difference between the phase of the first clock signal CLK and the phase of the second clock signal Clk/Sync. The charge pump 232 generates an analog signal on the basis of the digital signal. The loop filter 233 is electrically insulated from the charge pump 232 in the image output period. The loop filter 233 is electrically connected to the charge pump 232 on the basis of the second control signal in the blanking period. The loop filter 233 generates an analog voltage signal on the basis of the analog signal. The VCO 234 generates the first clock signal CLK on the basis of the analog voltage signal.

The switch 237 is electrically connected to the charge pump 232 and the loop filter 233. The switch 237 is turned off in the image output period and thus electrically insulates the loop filter 233 from the charge pump 232. The switch 237 is turned on in the blanking period and thus electrically connects the loop filter 233 to the charge pump 232.

The phase comparator 231 is connected to the frequency divider 235 and the switch 236. The first clock signal CLK is output from the frequency divider 235. The second clock signal Clk/Sync is output from the switch 236. The first clock signal CLK and the second clock signal Clk/Sync are input to the phase comparator 231. The phase comparator 231 generates a digital signal that represents the difference between the phase of the first clock signal CLK and the phase of the second clock signal Clk/Sync. The phase comparator 231 outputs the generated digital signal to the charge pump 232.

The charge pump 232 converts the digital signal into an analog signal. The charge pump 232 generates an analog voltage signal or an analog current signal on the basis of the digital signal. The charge pump 232 outputs the generated analog voltage signal or the generated analog current signal to the loop filter 233.

The loop filter 233 is a circuit including a capacitor and a resistor. The loop filter 233 accumulates electric charge that is based on the analog voltage signal or the analog current signal in the capacitor. The loop filter 233 generates an analog voltage signal on the basis of the electric charge accumulated in the capacitor. The loop filter 233 outputs the generated analog voltage signal to the VCO 234.

The VCO 234 generates the first clock signal CLK having the frequency that is based on the analog voltage signal. In this way, the VCO 234 generates the first clock signal CLK synchronized with the second clock signal Clk/Sync. The VCO 234 outputs the generated first clock signal CLK to the frequency divider 235.

The frequency divider 235 converts the frequency of the input first clock signal CLK into a lower frequency. The frequency divider 235 outputs the first clock signal CLK of which the frequency has been converted to the phase comparator 231 and the signal generation circuit 24.

The switch 236 is connected to the first signal line 31 and the phase comparator 231. The switch 236 is an element that is able to switch between an ON state and an OFF state. The state of the switch 236 becomes any one of the ON state and the OFF state. The state of the switch 236 is controlled on the basis of the second control signal Enable.

When the switch 236 is in the ON state, the first signal line 31 and the phase comparator 231 are electrically connected to each other. At this time, the second clock signal Clk/Sync is input to the phase comparator 231. When the switch 236 is in the OFF state, the first signal line 31 and the phase comparator 231 are electrically insulated from each other. At this time, input of the second clock signal Clk/Sync to the phase comparator 231 is stopped. The switch 236 is in the ON state in the blanking period and the switch 236 is in the OFF state in the image output period. The switch 236 may not be disposed.

The switch 237 is connected to the charge pump 232 and the loop filter 233. The switch 237 is an element that is able to switch between an ON state and an OFF state. The state of the switch 237 becomes any one of the ON state and the OFF state. The state of the switch 237 is controlled on the basis of the second control signal Enable.

When the switch 237 is in the ON state, the charge pump 232 and the loop filter 233 are electrically connected to each other. At this time, the analog signal is input to the loop filter 233. When the switch 237 is in the OFF state, the charge pump 232 and the loop filter 233 are electrically insulated from each other. At this time, input of the analog signal to the loop filter 233 is stopped. The switch 237 is in the ON state in the blanking period and the switch 237 is in the OFF state in the image output period.

The phase comparator 231 generates the digital signal in the blanking period. The charge pump 232 generates the analog signal in the blanking period. The loop filter 233 holds the analog voltage signal in the image output period. The VCO 234 generates the first clock signal CLK in the blanking period and the image output period.

A logical circuit 27 is disposed in the scope 20. An input terminal of the logical circuit 27 is electrically connected to the second signal line 32. An output terminal of the logical circuit 27 is electrically connected to the switch 236 and the switch 237. A threshold voltage of the logical circuit 27 is outside the range of the voltage of the second signal. The threshold voltage of the logical circuit 27 is within the range of the voltage of the second control signal Enable.

For example, the logical circuit 27 is an inverter. The second control signal Enable that has passed through the second signal line 32 is input to the logical circuit 27. The logical circuit 27 inverts the logical state of the second control signal Enable. The logical circuit 27 outputs the second control signal Enable to the switch 236 and the switch 237.

The voltage of the differential signal changes in a range from the maximum voltage to the minimum voltage. For example, the center voltage of the differential signal is half a power source voltage. For example, the maximum voltage of the differential signal is 150 mV greater than the center voltage and the minimum voltage of the differential signal is 150 mV less than the center voltage. When the power source voltage is at 1.8V, the center voltage is at 0.9V. In such a case, the voltage range of the differential signal is from 0.75V to 1.05V. The voltage of the differential signal is within this predetermined voltage range.

In the above-described example, the threshold voltage of the logical circuit 27 is less than 0.75V. For example, the threshold voltage of the logical circuit 27 is 0.6V. When the second control signal Enable is at a high level, the voltage of the second control signal Enable is greater than the threshold voltage of the logical circuit 27. When the second control signal Enable is at a low level, the voltage of the second control signal Enable is less than the threshold voltage of the logical circuit 27.

In the blanking period, the second control signal Enable of the low level is input to the logical circuit 27. The logical circuit 27 outputs the second control signal Enable of the high level to the switch 236 and the switch 237. The switch 236 and the switch 237 are turned on. The logical circuit 27 can keep the switch 236 and the switch 237 in the ON state in the blanking period.

When the blanking period is completed, the second control signal Enable of the high level is input to the logical circuit 27. The logical circuit 27 outputs the second control signal Enable of the low level to the switch 236 and the switch 237. The switch 236 and the switch 237 are turned off.

In the image output period, the second signal is input to the logical circuit 27. The minimum voltage of the second signal is greater than the threshold voltage of the logical circuit 27. For this reason, in the image output period, the second control signal Enable output from the logical circuit 27 is kept at the low level. The logical circuit 27 can keep the switch 236 and the switch 237 in the OFF state in the image output period.

Figure 4:
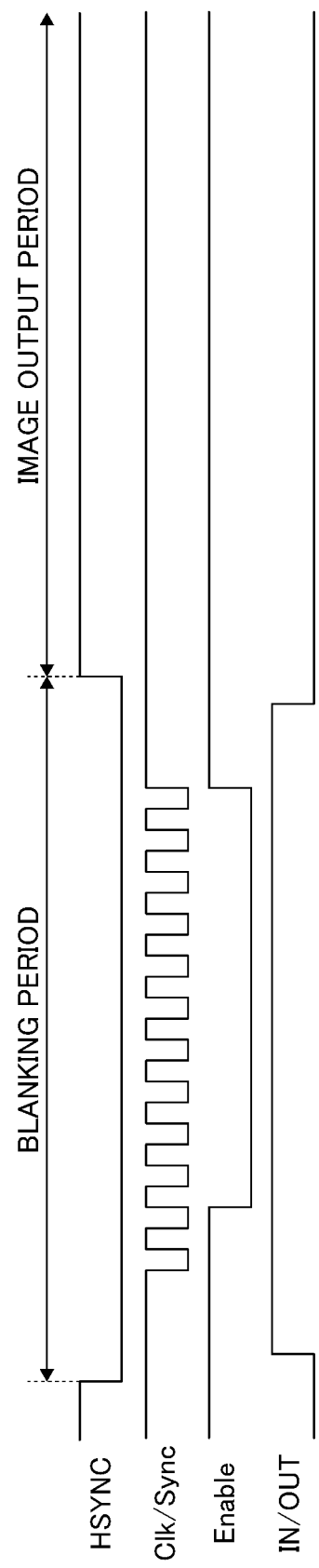
FIG. 4 is a timing chart showing a waveform of a main signal in the endoscope system according to the first embodiment of the present invention.

FIG. 4 shows a wavelength of a main signal used in the endoscope system 1. In FIG. 4, time passes in the right direction. In FIG. 4, the vertical direction represents voltage of each signal. In FIG. 4, a wavelength of each of a horizontal synchronizing signal HSYNC, the second clock signal Clk/Sync, the second control signal Enable, and the switching signal IN/OUT is shown.

The horizontal synchronizing signal HSYNC represents any one of the blanking period and the image output period. Before the blanking period is started, the second clock signal Clk/Sync and the second control signal Enable are at the high level. Before the blanking period is started, the switching signal IN/OUT is at the low level.

After the blanking period is started, the signal processing circuit 52 generates the switching signal IN/OUT of the high level. For this reason, the switch 533 and the switch 534 are turned on and the switch 55 and the switch 56 are turned off. Thereafter, the signal processing circuit 52 generates the second clock signal Clk/Sync and also generates the second control signal Enable of the low level. The signal output circuit 53 outputs the second clock signal Clk/Sync to the first signal line 31 and the second control signal Enable of the low level to the second signal line 32. The imaging device 21 stops generation of the image signal in the blanking period. The differential signal transmission circuit 22 stops transmission of the differential signal in the blanking period. The switch 236 and the switch 237 are turned on in the blanking period.

Since the switch 236 is in the ON state, the second clock signal Clk/Sync is input to the phase comparator 231. The phase comparator 231 outputs the digital signal that represents the phase difference to the charge pump 232. Since the switch 237 is in the ON state, the charge pump 232 and the loop filter 233 are electrically connected to each other. The charge pump 232 outputs the analog signal to the loop filter 233. The loop filter 233 holds the analog voltage signal. The VCO 234 generates the first clock signal CLK.

Before the blanking period is completed, the signal processing circuit 52 stops generation of the second clock signal Clk/Sync. Before the blanking period is completed, the signal processing circuit 52 generates the second control signal Enable of the high level. The signal output circuit 53 outputs the second control signal Enable of the high level to the second signal line 32. At this time, the switch 236 and the switch 237 are turned off. After generation of the second clock signal Clk/Sync is stopped and the second control signal Enable of the high level is output to the second signal line 32, the signal processing circuit 52 generates the switching signal IN/OUT of the low level. For this reason, the switch 533 and the switch 534 are turned off and the switch 55 and the switch 56 are turned on. After the switching signal IN/OUT becomes at the low level, the blanking period is completed.

When the blanking period is completed, the image output period is started. The imaging device 21 generates the image signal in the image output period. The differential signal transmission circuit 22 transmits the differential signal in the image output period. The switch 236 and the switch 237 are in the OFF state in the image output period.

Since the switch 236 is in the OFF state, the second clock signal Clk/Sync is not input to the phase comparator 231. Since the switch 237 is in the OFF state, the charge pump 232 and the loop filter 233 are electrically insulated from each other. In the image output period, the loop filter 233 continues to hold the analog voltage signal generated in the blanking period. The VCO 234 generates the first clock signal CLK.

When the image output period is completed, the blanking period is started. The blanking period and the image output period are repeated in turn.

When the image output period is completed, the differential signal transmission circuit 22 may transmit a differential signal including a code that represents start of the blanking period. The differential signal reception circuit 51 may detect the code on the basis of the received differential signal. When the differential signal reception circuit 51 detects the code, the signal output circuit 53 may start output of the second clock signal Clk/Sync and the second control signal Enable.

In the related art, three signal lines for transmitting an image signal, a reference clock signal, and a synchronizing signal are necessary. In the first embodiment of the present invention, a signal line for transmitting a synchronizing signal is unnecessary. In the first embodiment, the image signal, the second clock signal, and the second control signal are transmitted by two signal lines. In the first embodiment, the image signal is a differential signal including the first signal and the second signal. In the first embodiment, the first signal line 31 is used for transmitting the first signal and the second clock signal. In the first embodiment, the second signal line 32 is used for transmitting the second signal and the second control signal. Since each of the first signal line 31 and the second signal line 32 is used for transmitting a plurality of signals, the endoscope system 1 can reduce the number of signal lines. Since it is possible to make the transmission cable 3 thinner, the burden of a patient is reduced.

The switch 237 is turned on in the blanking period. At this time, the PLL 23 can generate the first clock signal synchronized with the second clock signal. The switch 237 is turned off in the image output period. Since the second clock signal is not input to the phase comparator 231 in the image output period, the phase comparator 231 and the charge pump 232 do not operate correctly. Since the switch 237 is in the OFF state, the state of the loop filter 233 is not influenced by the operation of the charge pump 232. In the image output period, the loop filter 233 continues to hold the analog voltage signal generated in the blanking period. The PLL 23 can consistently generate the first clock signal.

The threshold voltage of the logical circuit 27 is outside the range of the voltage of the second signal. The output voltage of the logical circuit 27 is fixed regardless of the change of the second signal in the image output period. For this reason, the switch 237 is kept in the OFF state in the image output period.

Second Embodiment

Figure 5:
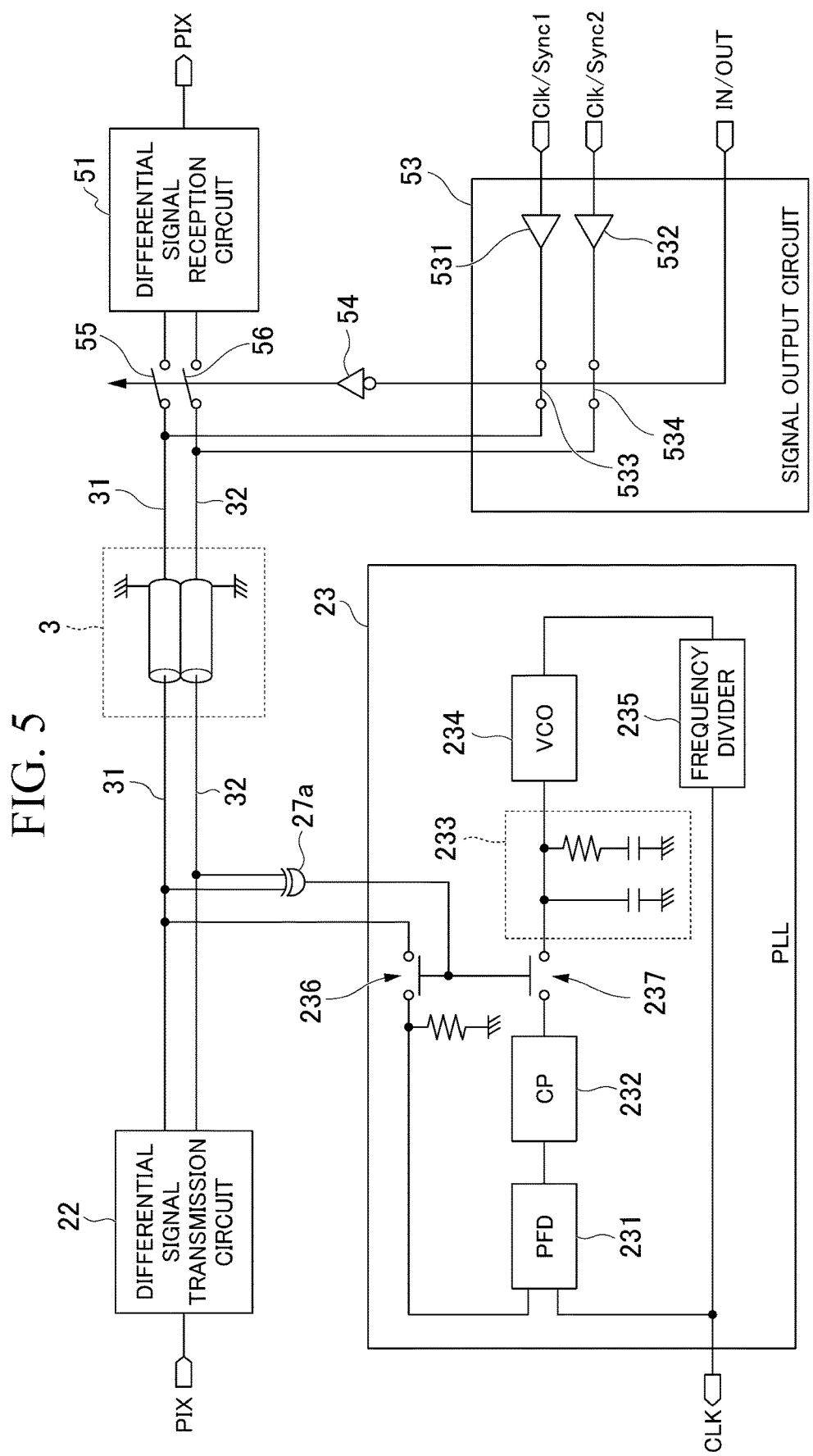
FIG. 5 is a block diagram showing a configuration of a main part of an endoscope system according to a second embodiment of the present invention.

FIG. 5 shows a configuration of a main part of an endoscope system 1 according to a second embodiment of the present invention. The same part as the part shown in FIG. 3 will not be described.

The signal output circuit 53 outputs a second clock signal Clk/Sync1 to the first signal line 31 in the blanking period. The signal output circuit 53 outputs a third clock signal Clk/Sync2 to the second signal line 32 in the blanking period. A logical circuit 27a (second signal generation circuit) generates the second control signal on the basis of the second clock signal Clk/Sync1 output to the first signal line 31 and the third clock signal Clk/Sync2 output to the second signal line 32.

The second clock signal Clk/Sync1 and the third clock signal Clk/Sync2 have logical states different from each other. When the second clock signal Clk/Sync1 is at the high level, the third clock signal Clk/Sync2 is at the low level. When the second clock signal Clk/Sync1 is at the low level, the third clock signal Clk/Sync2 is at the high level.

The signal processing circuit 52 generates the second clock signal Clk/Sync1 and the third clock signal Clk/Sync2. For example, the signal processing circuit 52 generates the third clock signal Clk/Sync2 by delaying the phase of the second clock signal Clk/Sync1. The signal processing circuit 52 may generate the second clock signal Clk/Sync1 by delaying the phase of the third clock signal Clk/Sync2. The signal processing circuit 52 may generate the third clock signal Clk/Sync2 by inverting the logical state of the second clock signal Clk/Sync1. The signal processing circuit 52 may generate the second clock signal Clk/Sync1 by inverting the logical state of the third clock signal Clk/Sync2. The signal processing circuit 52 outputs the second clock signal Clk/Sync1 and the third clock signal Clk/Sync2 to the signal output circuit 53.

The second clock signal Clk/Sync1 is input to the buffer 531. The third clock signal Clk/Sync2 is input to the buffer 532. The buffer 531 outputs the second clock signal Clk/Sync1 to the switch 533. The buffer 532 outputs the third clock signal Clk/Sync2 to the switch 534. When the switch 533 is in the ON state, the second clock signal Clk/Sync1 is output to the first signal line 31. When the switch 534 is in the ON state, the third clock signal Clk/Sync2 is output to the second signal line 32.

The logical circuit 27 shown in FIG. 3 is changed to the logical circuit 27a. The logical circuit 27a is an XOR circuit. A first input terminal of the logical circuit 27a is electrically connected to the first signal line 31. A second input terminal of the logical circuit 27a is electrically connected to the second signal line 32. An output terminal of the logical circuit 27a is electrically connected to the switch 236 and the switch 237. The second clock signal Clk/Sync1 that has passed through the first signal line 31 is input to the logical circuit 27a. The third clock signal Clk/Sync2 that has passed through the second signal line 32 is input to the logical circuit 27a.

When the logical states of the two input terminals of the logical circuit 27a are different from each other, the logical circuit 27a outputs the second control signal of the high level to the switch 236 and the switch 237. When the logical states of the two input terminals of the logical circuit 27a are the same, the logical circuit 27a outputs the second control signal of the low level to the switch 236 and the switch 237.

A threshold voltage of the logical circuit 27a is outside the range of the voltage of the first signal and the second signal. The threshold voltage of the logical circuit 27a is within the range of the voltage of the second clock signal Clk/Sync1 and the third clock signal Clk/Sync2.

In the blanking period, the second clock signal Clk/Sync1 and the third clock signal Clk/Sync2 are input to the logical circuit 27a. The logical states of the second clock signal Clk/Sync1 and the third clock signal Clk/Sync2 are different from each other. For this reason, the logical circuit 27a outputs the second control signal of the high level to the switch 236 and the switch 237. The switch 236 and the switch 237 are turned on. The logical circuit 27a can keep the switch 236 and the switch 237 in the ON state in the blanking period.

When the blanking period is completed, the second clock signal Clk/Sync1 of the high level and the third clock signal Clk/Sync2 of the high level are input to the logical circuit 27a. The logical states of the second clock signal Clk/Sync1 and the third clock signal Clk/Sync2 are the same. For this reason, the logical circuit 27a outputs the second control signal of the low level to the switch 236 and the switch 237. The switch 236 and the switch 237 are turned off.

In the image output period, the second signal is input to the logical circuit 27a. The minimum voltage of the second signal is greater than the threshold voltage of the logical circuit 27a. For this reason, in the image output period, the second control signal output from the logical circuit 27a is kept at the low level. The logical circuit 27a can keep the switch 236 and the switch 237 in the OFF state in the image output period.

Figure 6:
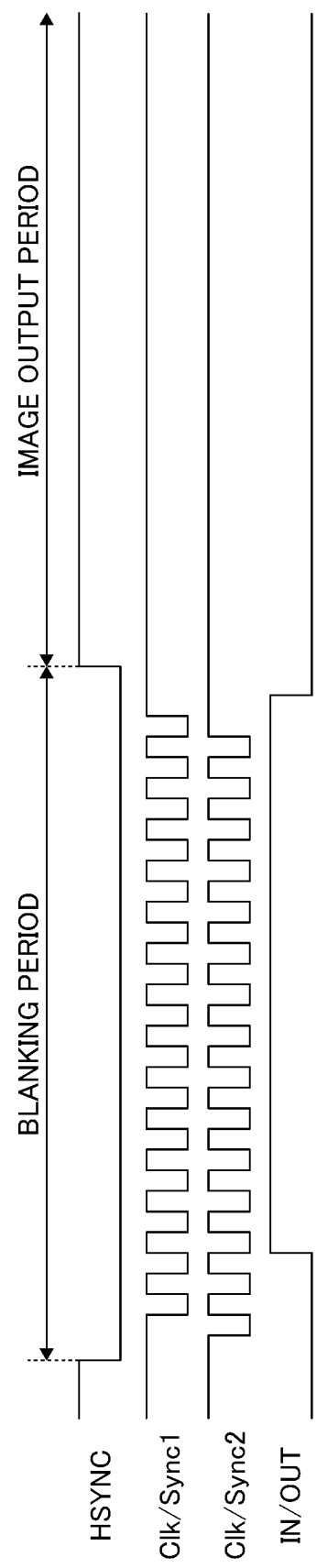
FIG. 6 is a timing chart showing a waveform of a main signal in the endoscope system according to the second embodiment of the present invention.

FIG. 6 shows a wavelength of a main signal used in the endoscope system 1. In FIG. 6, time passes in the right direction. In FIG. 6, the vertical direction represents voltage of each signal. In FIG. 6, a wavelength of each of the horizontal synchronizing signal HSYNC, the second clock signal Clk/Sync1, the third clock signal Clk/Sync2, and the switching signal IN/OUT is shown. The description same as the description regarding FIG. 4 will be omitted.

Before the blanking period is started, the second clock signal Clk/Sync1 and the third clock signal Clk/Sync2 are at the high level. Before the blanking period is started, the switching signal IN/OUT is at the low level.

After the blanking period is started, the signal processing circuit 52 generates the second clock signal Clk/Sync1 and the third clock signal Clk/Sync2. Thereafter, the signal processing circuit 52 generates the switching signal IN/OUT of the high level. For this reason, the switch 533 and the switch 534 are turned on and the switch 55 and the switch 56 are turned off. The signal output circuit 53 outputs the second clock signal Clk/Sync1 to the first signal line 31 and the third clock signal Clk/Sync2 to the second signal line 32. The switch 236 and the switch 237 are turned on in the blanking period.

Before the blanking period is completed, the signal processing circuit 52 stops generation of the second clock signal Clk/Sync1 and the third clock signal Clk/Sync2. The signal output circuit 53 outputs the second clock signal Clk/Sync1 of the high level to the first signal line 31 and outputs the third clock signal Clk/Sync2 of the high level to the second signal line 32. At this time, the switch 236 and the switch 237 are turned off After generation of the second clock signal Clk/Sync1 and the third clock signal Clk/Sync2 is stopped, the signal processing circuit 52 generates the switching signal IN/OUT of the low level. For this reason, the switch 533 and the switch 534 are turned off and the switch 55 and the switch 56 are turned on. After the switching signal IN/OUT becomes at the low level, the blanking period is completed.

In the second embodiment, as with the first embodiment, each of the first signal line 31 and the second signal line 32 is used for transmitting a plurality of signals. For this reason, the endoscope system 1 can reduce the number of signal lines.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging system comprising:
a camera unit; and
a main body,
wherein the camera unit includes:
 a phase locked loop (PLL) configured to generate a first clock signal;
 a signal generation circuit configured to generate a first control signal on the basis of the first clock signal;
 a solid-state imaging device configured to generate an image signal on the basis of the first control signal; and
 a differential signal transmission circuit configured to output a first signal generated on the basis of the image signal to a first signal line in an image output period and configured to output a second signal generated on the basis of the image signal to a second signal line different from the first signal line in the image output period, the first signal and the second signal being included in a differential signal,
the main body includes:
 a differential signal reception circuit configured to receive the first signal output to the first signal line and the second signal output to the second signal line; and
 a signal output circuit configured to output a second clock signal to the first signal line in a blanking period different from the image output period and configured to output a second control signal to the second signal line in the blanking period,
the PLL includes:
 a phase comparator;
 a charge pump;
 a loop filter; and
 a voltage-controlled oscillator,
the second clock signal output to the first signal line is input to the phase comparator,
the phase comparator is configured to compare a phase of the first clock signal with a phase of the second clock signal and is configured to generate a digital signal that represents a difference between the phase of the first clock signal and the phase of the second clock signal,
the charge pump is configured to generate an analog signal on the basis of the digital signal,
the loop filter is electrically insulated from the charge pump in the image output period,
the loop filter is electrically connected to the charge pump in the blanking period on the basis of the second control signal output to the second signal line,
the loop filter is configured to generate an analog voltage signal on the basis of the analog signal, and
the voltage-controlled oscillator is configured to generate the first clock signal on the basis of the analog voltage signal.

2. The imaging system according to claim 1,
wherein the PLL further includes a switch electrically connected to the charge pump and the loop filter,
the switch is configured to be turned off in the image output period and thus electrically insulate the loop filter from the charge pump, and
the switch is configured to be turned on in the blanking period and thus electrically connect the loop filter to the charge pump.

3. The imaging system according to claim 2, further comprising a logical circuit electrically connected to the switch and the second signal line,
wherein a threshold voltage of the logical circuit is outside a range of a voltage of the second signal.

4. The imaging system according to claim 1,
wherein the phase comparator is configured to generate the digital signal in the blanking period,
the charge pump is configured to generate the analog signal in the blanking period,
the loop filter is configured to hold the analog voltage signal in the image output period, and
the voltage-controlled oscillator is configured to generate the first clock signal in the blanking period and the image output period.

5. An endoscope system comprising:
a scope including a tip end and a base end; and
the imaging system according to claim 1,
wherein the solid-state imaging device is disposed in the tip end, and
the main body is connected to the base end.

6. An imaging system comprising:
a camera unit; and
a main body,
wherein the camera unit includes:
a phase locked loop (PLL) configured to generate a first clock signal;
a first signal generation circuit configured to generate a first control signal on the basis of the first clock signal;
a solid-state imaging device configured to generate an image signal on the basis of the first control signal;
a differential signal transmission circuit configured to output a first signal generated on the basis of the image signal to a first signal line in an image output period and configured to output a second signal generated on the basis of the image signal to a second signal line different from the first signal line in the image output period, the first signal and the second signal being included in a differential signal; and
a second signal generation circuit,
the main body includes:
a differential signal reception circuit configured to receive the first signal output to the first signal line and the second signal output to the second signal line; and
a signal output circuit configured to output a second clock signal to the first signal line in a blanking period different from the image output period and configured to output a third clock signal to the second signal line in the blanking period,
the second signal generation circuit is configured to generate a second control signal on the basis of the second clock signal output to the first signal line and the third clock signal output to the second signal line,
the PLL includes:
a phase comparator;
a charge pump;
a loop filter; and
a voltage-controlled oscillator,
the second clock signal output to the first signal line is input to the phase comparator,
the phase comparator is configured to compare a phase of the first clock signal with a phase of the second clock signal and is configured to generate a digital signal that represents a difference between the phase of the first clock signal and the phase of the second clock signal,
the charge pump is configured to generate an analog signal on the basis of the digital signal,
the loop filter is electrically insulated from the charge pump in the image output period,
the loop filter is electrically connected to the charge pump in the blanking period on the basis of the second control signal,
the loop filter is configured to generate an analog voltage signal on the basis of the analog signal, and
the voltage-controlled oscillator is configured to generate the first clock signal on the basis of the analog voltage signal.

7. The imaging system according to claim 6,
wherein the PLL further includes a switch electrically connected to the charge pump and the loop filter,
the switch is configured to be turned off in the image output period and thus electrically insulate the loop filter from the charge pump, and
the switch is configured to be turned on in the blanking period and thus electrically connect the loop filter to the charge pump.

8. The imaging system according to claim 7, further comprising a logical circuit electrically connected to the switch and the second signal line,
wherein a threshold voltage of the logical circuit is outside a range of a voltage of the first signal and the second signal.

9. The imaging system according to claim 6,
wherein the phase comparator is configured to generate the digital signal in the blanking period,
the charge pump is configured to generate the analog signal in the blanking period,
the loop filter is configured to hold the analog voltage signal in the image output period, and
the voltage-controlled oscillator is configured to generate the first clock signal in the blanking period and the image output period.

* * * * *